United States Patent [19]

Takaya et al.

[11] Patent Number: 4,496,562
[45] Date of Patent: Jan. 29, 1985

[54] 7-SUBSTITUTED-3-CEPHEM-4-CARBOXYLIC ACID ESTERS

[75] Inventors: Takao Takaya, Kawanishi; Hisashi Takasugi, Osaka; Kiyoshi Tsuji, Kishiwada; Toshiyuki Chiba, Osaka, all of Japan

[73] Assignee: Fujisawa Pharmaceutical Co., Ltd., Osaka, Japan

[21] Appl. No.: 447,218

[22] Filed: Dec. 6, 1982

Related U.S. Application Data

[63] Continuation-in-part of Ser. No. 886,340, Mar. 14, 1978, Pat. No. 4,425,341.

[51] Int. Cl.$^3$ ............... C07D 501/22; A61K 31/545
[52] U.S. Cl. ..................... 514/207; 544/16; 544/21; 544/22
[58] Field of Search .............. 544/21, 22, 26, 27; 424/246

[56] References Cited

U.S. PATENT DOCUMENTS 4,399,131 8/1983 Dürckheimer et al. ............ 544/21

Primary Examiner—Nicholas S. Rizzo
Attorney, Agent, or Firm—Oblon, Fisher, Spivak, McClelland & Maier

[57] ABSTRACT

There are disclosed compounds of the formula:

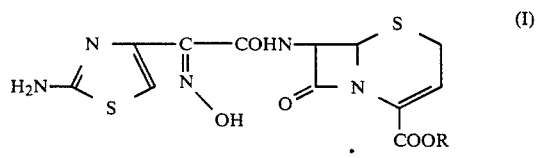

in which R is lower alkoxycarbonyloxy(lower)alkyl or 1-propionyloxyethyl, or a salt thereof, pharmaceutical compositions containing the same and their use to treat infectious diseases.

6 Claims, No Drawings

7-SUBSTITUTED-3-CEPHEM-4-CARBOXYLIC ACID ESTERS

The present application is a continuation-in-part of application Ser. No. 886,340, filed Mar. 14, 1978 now U.S. Pat. No. 4,425,341.

The present invention relates to novel 7-substituted-3-cephem-4-carboxylic acid esters and a salt thereof.

More particularly, it relates to novel 7-substituted-3-cephem-4-carboxylic acid esters and a salt thereof, which have antimicrobial activity, to a process for production of the same, to a pharmaceutical composition comprising the same, and to a method for treatment of infectious diseases caused by pathogenic microorganisms which comprises administering the same to infected human being or animals.

Accordingly, one object of the present invention is to provide novel 7-substituted-3-cephem-4-carboxylic acid esters and a salt thereof, which are highly active against a number of pathogenic microorganisms and are useful as antimicrobial agents, especially for oral administration.

Another object of the present invention is to provide a process for production of novel 7-substituted-3-cephem-4-carboxylic acid esters and a salt thereof.

A further object of the present invention is to provide a pharmaceutical composition comprising, as an active ingredient, said 7-substituted-3-cephem-4-carboxylic acid esters and a pharmaceutically acceptable salt thereof.

Still further object of the present invention is to provide a method for the treatment of infectious diseases caused by pathogenic microorganisms which comprises administering said 7-substituted-3-cephem-4-carboxylic acid esters and a pharmaceutically acceptable salt thereof to the infected human being or animals.

The 7-substituted-3-cephem-4-carboxylic acid esters according to this invention are novel and can be represented by the following general formula:

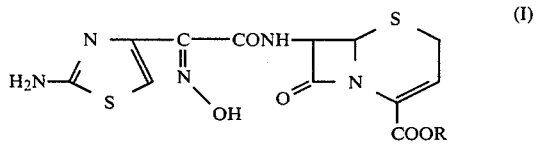

in which R is lower alkoxycarbonyloxy(lower)alkyl or 1-propionyloxyethyl.

In the object compound (I) and the corresponding starting compounds (II) to (IV) in Processes 1 and 2 mentioned below, it is to be understood that there may be one or more stereoisomeric pairs such as optical isomers due to asymmetric carbon atom in their molecules and such isomers are also included within the scope of the present invention.

Further, it is to be understood that the term "syn isomer" used in the present specification means the compound having the stereospecific partial structure of the formula

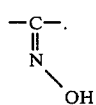

Suitable salt of the object compound (I) may include any pharmaceutically acceptable salt, for example, acid addition salt such as an inorganic acid addition salt (e.g. hydrochloride, hydrobromide, sulfate, phosphate, etc.), an organic carboxylic acid or sulfonic acid addition salt (e.g. formate, acetate, trifluoroacetate, fumarate, citrate, maleate, tartarate, methanesulfonate, benzenesulfonate, p-toluenesulfonate, etc.), an acidic amino acid salt (e.g. aspartic acid salt, glutamic acid salt, etc.), or the like.

The object compound (I) or a salt thereof of this invention can be produced by the processes illustrated below.

(1) Process 1: Esterification

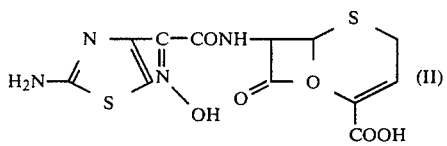

or a reactive derivative at the carboxy group thereof, or a salt thereof

R—OH (III)
or a reactive derivative at the hydroxy group thereof

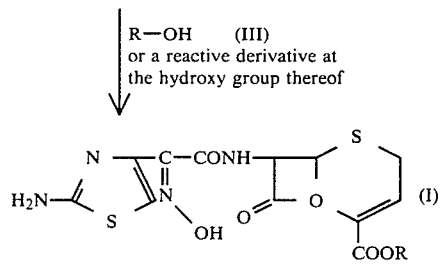

or a salt thereof (2) Process 2: Thiazole Ring Formation

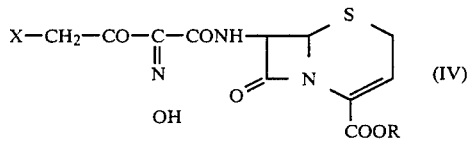

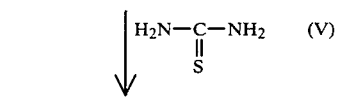

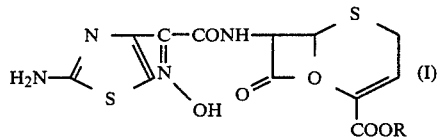

or a salt thereof in which
X is halogen and
R is as defined above.

In the above description of the present specification, suitable examples and illustration of the definitions to be included within the scope thereof are explained in details as follows.

Suitable "lower alkoxycarbonyloxy(lower)alkyl" for R may include straight or branched one having up to 6 carbon atoms in each alkyl moiety thereof, such as methoxycarbonyloxymethyl, ethoxycarbonyloxymethyl, propoxycarbonyloxymethyl, isopropoxycarbonyloxymethyl, tert-butoxycarbonyloxymethyl, 1- or 2-methoxycarbonyloxyethyl, 1- or 2-ethoxycarbonyloxyethyl, 1- or 2-propoxycarbonyloxyethyl, - or 2-isopropoxycarbonyloxyethyl, 1- or 2-butoxycarbonyloxyethyl, 1- or 2-isobutoxycarbonyloxyethyl, 1- or 2-tert-butoxycarbonyloxyethyl, 1- or 2-hexyloxycarbonyloxyethyl, 1- or 2- or 3-methoxycarbonyloxypropyl, 1- or 2- or 3-ethoxycarbonyloxypropyl, 1- or 2- or 3-isopropoxycarbonyloxypropyl, 1- or 2- or 3- or 4-ethoxycarbonyloxybutyl, 1- or 2- or 3- or 4-butoxycarbonyloxybutyl, 1- or 2- or 3- or 4- or 5-pentyloxycarbonyloxypentyl, 1- or 2- or 3- or 4- or 5-neopentyloxycarbonyloxypentyl, 1- or 2- or 3- or 4- or 5- or 6-ethoxycarbonyloxyhexyl, or the like, in which the preferred one is 1-($C_1$–$C_6$)alkoxycarbonyloxy($C_1$–$C_6$)alkyl and the more preferred one is 1-($C_1$–$C_3$)alkoxycarbonyloxy($C_1$–$C_3$)alkyl and the most preferred one is 1-ethoxycarbonyloxyethyl.

Suitable "halogen" for X may include chlorine, bromine, iodine and the like.

The processes for the production of the compound (I) or a salt thereof will be explained in detail as follows.

(1) Process 1: Esterification

The compound (I) or a salt thereof can be produced by esterifying the compound (II) or a reactive derivative at the carboxy group thereof, or a salt thereof with the compound (III) or a reactive derivative at the hydroxy group thereof.

Suitable reactive derivative at the carboxy group of the compound (II) may include conventional one which can be applied to esterification of a carboxy group such as acid halide (e.g. acid chloride, acid bromide, etc.), or the like.

Suitable salt of the compound (II) and a reactive derivative at the carboxy group thereof may include an acid addition salt as mentioned above and additionally a salt with a base, i.e., an inorganic or organic base salt such as an alkali metal salt (e.g. sodium salt, potassium salt, etc.), an alkaline earth metal salt (e.g. calcium salt, magnesium salt, etc.), ammonium salt, salt with an amine, for example, alkylamine salt (e.g. methylamine salt, triethylamine salt, pyridine salt, etc.), or the like.

Suitable reactive derivative at the hydroxy group of the compound (III) may include the compound (III) whose hydroxy group is substituted by an acid residue such as halogen (e.g. chlorine, bromine, iodine, etc.), or the like, and additionally basic salts of the compound (III) such as those aforementioned.

The present invention is usually conducted in the presence of an organic or inorganic base such as alkali metal (e.g. lithium, sodium, potassium, etc.), alkaline earth metal (e.g. calcium, etc.), alkali metal hydride (e.g. sodium hydride, etc.), alkaline earth metal hydride (e.g. calcium hydride, etc.), alkali metal hydroxide (e.g. sodium hydroxide, potassium hydroxide, etc.), alkali metal carbonate (e.g. sodium carbonate, potassium carbonate, etc.), alkali metal bicarbonate (e.g. sodium bicarbonate, potassium bicarbonate, etc.), alkali metal alkoxide (e.g. sodium methoxide, sodium ethoxide, potassium tert-butoxide, etc.), alkali metal alkanoate (e.g. sodium acetate, etc.), trialkylamine (e.g. triethylamine, etc.), pyridines (e.g. pyridine, lutidine, picoline, etc.), quinoline and the like, and in case that the reactive derivative at the hydroxy group of the compound (III) is a halide other than the iodide, the reaction is often conducted in the presence of a metal iodide such as sodium iodide.

In this reaction, in case that the compound (III) is used in a free form, the reaction is preferably conducted in the presence of a condensing agent which is generally employed for esterification such as a carbodiimide compound [e.g. N,N'-dicyclohexylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.], diazabicyclo compound (1,8-diazabicyclo[5.4.0]undec-7-ene, 1,4-diazabicyclo[2.2.2]octane, etc.), a sulfonic acid ester of N-hydroxybenzotriazole derivative [e.g. 1-(4-chlorobenzenesulfonyloxy)-6-chloro-1H-benzotriazole, etc.], or the like.

This reaction is usually conducted in a conventional solvent which does not adversely influence the reaction such as acetone, dioxane, acetonitrile, chloroform, benzene, dichloromethane, ethylene chloride, tetrahydrofuran, ethyl acetate, dimethylsulfoxide, N,N-dimethylformamide, N,N-dimethylacetamide, pyridine, hexamethylphosphoramide, etc. or a mixture thereof.

The reaction temperature is not critical, and the reaction is in many cases conducted under cooling, at ambient temperature or under heating.

(2) Process 2: Thiazole Ring Formation

The compound (I) or a salt thereof can be produced by reacting the compound (IV) with thiourea (V).

This reaction is usually conducted in a conventional solvent which does not adversely influence the reaction such as ethyl acetate, dichloromethane, chloroform, carbon tetrachloride, tetrahydrofuran, methanol, ethanol, dioxane, water, etc., or a mixture thereof.

The reaction temperature is not critical and the reaction is usually conducted under from cooling to heating.

The object compound (I) thus obtained can be isolated in a conventional manner, and if necessary, converted to its salt in a conventional manner.

The object compound (I) and the salt thereof of the present invention are novel and exhibit high antimicrobial activity, inhibiting the growth of a wide variety of pathogenic microorganisms including Gram-positive and Gram-negative microorganisms and are useful as anti-microbial agents, especially for oral administration.

Now in order to show the utility of the object compound (I), the test data on the urinary excretion of some representative compound (I) of this invention are shown in the following.

Urinary Excretion Test (1) Test Method

Test compound (100 mg/kg) was given orally to groups of three rats, and urinary samples were collected at 0 to 24 hours.

(2) Test Compound

1-DL-Ethoxycarbonyloxyethyl 7-[2-(2-aminothiazol-4-yl)-2-hydroxyiminoacetamido]-3-cephem-4-carboxylate (syn isomer)

(3) Test Results

Percentage of urinary excretion value was shown in the following table.

| Urinary Excretion (%) |
| --- |
| 35.0 |

For therapeutic administration, the object compound (I) and the pharmaceutically acceptable salt thereof of the present invention are used in the form of conventional pharmaceutical preparation which contains said compound as an active ingredient, in admixture with pharmaceutically acceptable carriers such as an organic or inorganic solid or liquid excipient which is suitable for oral, parenteral and external administration. The pharmaceutical preparations may be in solid form such as tablet, granule, powder, capsule, or liquid form such as solution, suspension, syrup, emulsion, lemonade and the like.

If needed, there may be included in the above preparations auxiliary substances, stabilizing agents, wetting agents and other commonly used additives such as lactose, fumaric acid, maleic acid, malic acid, succinic acid, citric acid, tartaric acid, stearic acid, magnesium stearate, terra alba, sucrose, corn starch, talc, gelatin, agar, pectin, peanut oil, olive oil, cacao butter, ethylene glycol, and the like.

While the dosage of the compound (I) may vary from and also depend upon the age, conditions of the patient, a kind of diseases, a kind of the compound (I) to be applied, etc. In general, amounts between 1 mg and about 4,000 mg or even more per day may be administered to a patient. An average single dose of about 50 mg, 100 mg, 250 mg, 500 mg, 1000 mg, 2000 mg of the object compound (I) of the present invention may be used in treating diseases infected by pathogenic microorganisms.

With regard to the starting compounds (II) and (IV) used in Processes 1 and 2, the compounds (II) is known, but the compound (IV) is new and can be prepared, for example, by the following method.

Preparation of Compound (IV)

Method 1:

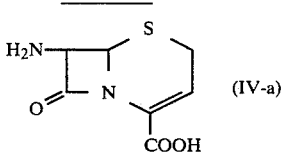
(IV-a)

or a reactive derivative at the carboxy group thereof, or a salt thereof

R—OH (III)
or a reactive derivative at the hydroxy group thereof

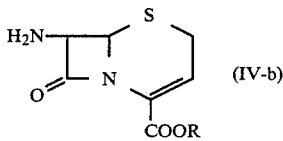
(IV-b)

or a salt thereof

Method 2:

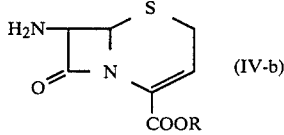
(IV-b)

or a reactive derivative at the amino group thereof or a salt thereof

Activated Acid formed by diketene and halogen

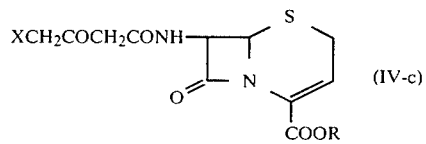
(IV-c)

Method 3:

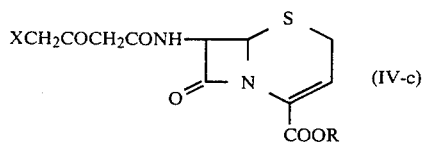
(IV-c)

Nitrosating Agent

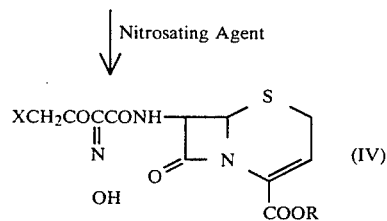
(IV)

in which R and X are each as defined above.

Explanation of Methods 1 to 3

Method 1:

The compound (IV-b) or a salt thereof can be produced by esterifying the compound (IV-a) or a reactive derivative at the carboxy group thereof, or a salt thereof with the compound (III) or a reactive derivative at the hydroxy group thereof.

Suitable reactive derivative at the carboxy group of the compound (IV-a) may include the same one as that of the compound (II).

Suitable salt of the compound (IV-a) may include the same one as that of the compound (II), and suitable salt of the compound (IV-b) may include the same one as that of the compound (I).

This esterification can be carried out in substantially the same manner as that of Process 1, and therefore the reaction conditions (e.g. base, condensing agent, solvent, reaction temperature, etc.) and the like can be referred to those of Process 1.

Method 2:

The compound (IV-c) can be produced by reacting the compound (IV-b) or a reactive derivative at the amino group thereof or a salt thereof with an activated acid formed by diketene and halogen.

Suitable reactive derivative at the amino group of the compound (IV-b) may include a silyl derivative formed by the reaction of the compound (IV-b) with a silyl compound (e.g. trimethylsilylacetamide, bis(trimethylsilyl)acetamide, etc.).

Suitable salt of the compound (IV-b) may include the same acid addition salt as aforementioned.

This reaction is usually conducted in a conventional solvent which does not adversely influence the reaction such as ethyl acetate, dichloromethane, chloroform, carbon tetrachloride, tetrahydrofuran, dioxane, water, etc., or a mixture thereof.

The reaction temperature is not critical and the reaction is usually conducted under from cooling to warming.

Method 3:

The compound (IV) can be produced by reacting the compound (IV-c) with a nitrosating agent.

Suitable nitrosating agent may include a conventional one which is applicable for conversion of a methylene group to a hydroxyiminomethylene group, for example, nitrous acid and its conventional derivatives such as nitrosyl halide (e.g. nitrosyl chloride, nitrosyl bromide, etc.), alkali metal nitrite (e.g. sodium nitrite, potassium nitrite, etc.), alkyl nitrite (e.g. butyl nitrite, pentyl nitrite, etc.) and the like.

In case that the alkali metal nitrite is used as a nitrosating agent, the reaction is preferably conducted in the presence of an acid such as an inorganic or organic acid (e.g. hydrochloric acid, sulfuric acid, formic acid, acetic acid, etc.).

This reaction is usually conducted in a conventional solvent which does not adversely influence the reaction such as water, acetic acid, benzene, methanol, ethanol, tetrahydrofuran, etc. or a mixture thereof.

The reaction temperature is not critical and the reaction is preferably conducted under from cooling to an ambient temperature.

The following examples are given for the purpose of illustrating the present invention.

EXAMPLE 1

To an ice-cooled aqueous solution of sodium bicarbonate (1.3 g) in water (50 ml) was added 7-[2-(2-aminothiazol-4-yl)-2-hydroxyiminoacetamido]-3-cephem-4-carboxylic acid (syn isomer)(1.2 g) under stirring. The resultant solution was lyophilized to give sodium salt of the above compound. This compound was dissolved in N,N-dimethylformamide (20 ml), and thereto was added 1-D,L-iodoethyl ethyl carbonate (0.97 g) at 0° to 5° C. under stirring. After stirring was continued at ambient temperature for 30 minutes, the reaction mixture was added to a mixture of ethyl acetate (100 ml) and water (50 ml). The separated organic layer was washed with water, a saturated aqueous sodium bicarbonate and an aqueous sodium chloride in turn. Removal of the solvent gave the residue, which was chromatographed on silica gel to give 1-D,L-ethoxycarbonyloxyethyl 7-[2-(2-aminothiazol-4-yl)-2-hydroxyiminoacetamido]-3-cephem-4-carboxylate (syn isomer)(0.5 g).

IR (Nujol): 3300 (broad), 1780–1750, 1670, 1620, 1520 cm$^{-1}$.

NMR (DMSO-d$_6$)δ: 1.2 (3H, t, J=8 Hz), 1.48 (3H, d, J=6 Hz), 3.5–3.8 (2H, m), 4.20 (2H, q, J=8 Hz), 5.11 (1H, d, J=5 Hz), 5.82 (1H, d, J=5,8 Hz), 6.68 (1H, s), 7.05 (2H, broad s), 9.45 (1H, d, J=8 Hz), 11.6 (1H, s).

EXAMPLE 2

1-D,L-Propionyloxyethyl 7-[2-(2-aminothiazol-4-yl)-2-hydroxyiminoacetamido]-3-cephem-4-carboxylate (syn isomer) was obtained by reacting 7-[2-(2-aminothiazol-4-yl)-2-hydroxyiminoacetamido]-3-cephem-4-carboxylic acid (syn isomer) with 1-D,L-chloroethyl propionate according to a similar manner to that of Example 1.

IR (Nujol): 3270, 1780, 1745, 1660 cm$^{-1}$.

EXAMPLE 3

(1) To a suspension of 7-amino-3-cephem-4-carboxylic acid (60 g) in N,N-dimethylacetamide (600 ml) was added 1,8-diazabicyclo[5,4,0]undec-7-ene (54.81 g) at ambient temperature, and the mixture was stirred at ambient temperature for 30 minutes. To this solution was added 1-D,L-iodoethyl ethyl carbonate (87.85 g) under ice-cooling and the reaction mixture was stirred at the same temperature for an hour. The reaction mixture was added to a mixture of water and ethyl acetate, and the separated organic layer was washed with a saturated aqueous sodium carbonate, water and an aqueous sodium chloride in turn, and dried over magnesium sulfate. Removal of the solvent gave 1-D,L-ethoxycarbonyloxyethyl 7-amino-3-cephem-4-carboxylate (42.1 g).

IR (Nujol): 1780, 1750 cm$^{-1}$.

NMR (DMSO-d$_6$) δ: 1.20 (3H, t, J=8 Hz), 1.47 (3H, d, J=5 Hz), 3.37–3.80 (2H, m), 4.20 (2H, q, J=8 Hz), 4.82 (1H, d, J=5 Hz), 4.95 (1H, d, J=5 Hz), 6.53 (1H, t, J=5 Hz), 6.73 (1H, q, J=5 Hz).

(2) To a solution of diketene (13.34 g) in dichloromethane (120 ml) was added a solution of bromine (8.95 ml) in dichloromethane (9 ml) at −20° C., and the mixture was stirred at the same temperature for 30 minutes. The resultant activated acid solution was added to a solution of 1-D,L-ethoxycarbonyloxyethyl 7-amino-3-cephem-4-carboxylate (42 g) and N-trimethylsilylacetamide (104.2 g) in ethyl acetate (420 ml) at −30° C. under stirring, and stirring was continued at −10° C. for 30 minutes. The reaction mixture was poured into water and then extracted with ethyl acetate. The extract was washed with a saturated aqueous sodium carbonate and an aqueous sodium chloride, followed by drying over magnesium sulfate. Removal of the solvent gave 1-D,L-ethoxycarbonyloxyethyl 7-(4-bromoacetoacetamido)-3-cephem-4-carboxylate, which was dissolved in dichloromethane (253 ml) and acetic acid (84 ml). To this solution was added a solution of sodium nitrite (7.28 g) in water (15 ml) at −10° C., followed by stirring at the same temperature for 10 minutes. The reaction mixture was poured into water and then extracted with dichloromethane. The extract was washed with a saturated aqueous sodium carbonate, water and an aqueous sodium chloride in turn and dried over magnesium sulfate. Removal of the solvent gave 1-D,L-ethoxycarbonyloxyethyl 7-(4-bromo-2-hydroxyiminoacetoacetamido)-3-cephem-4-carboxylate, which was dissolved in tetrahydrofuran (100 ml) and ethanol (100 ml). To the resultant solution was added thiourea (6.41 g), followed by stirring at ambient temperature for an hour. The reaction mixture was evaporated in vacuo and to the residue were added ethyl acetate and water. The separated ethyl acetate layer was washed with an aqueous sodium chloride and dried over magnesium sulfate. Removal of the solvent gave a residue, which was chromatographed on silica gel for purification to obtain 1-D,L-ethoxycarbonyloxyethyl 7-[2-(2-aminothiazol-4-yl)-2-hydroxyiminoacetamido]-3-cephem-4-carboxylate (syn isomer)(7.20 g).

IR (Nujol): 3300 (broad), 1780–1750, 1670, 1620, 1520 cm$^{-1}$.

EXAMPLE 4

(1) 1-D,L-Propionyloxyethyl 7-amino-3-cephem-4-carboxylate (20.8 g) was prepared by reacting 7-amino-3-cephem-4-carboxylic acid (40 g) with 1-D,L-chloroethyl propionate (32.78 g) in the presence of potassium carbonate (16.59 g) according to a similar manner to that of Example 3-(1).

IR (Film): 1780, 1750 cm$^{-1}$.

NMR (DMSO-d$_6$) δ: 0.98 (3H, t, J=7 Hz), 1.42 (3H, d, J=6 Hz), 2.25 (2H, q, J=7 Hz), 3.22–3.70 (2H, m), 4.88 (1H, d, J=4 Hz), 5.03 (1H, d, J=4 Hz), 6.58 (1H, t, J=5 Hz), 6.87 (1H, q, J=6 Hz).

(2) 1-D,L-Propionyloxyethyl 7-[2-(2-aminothiazol-4-yl)-2-hydroxyiminoacetamido]-3-cephem-4-carboxylate (syn isomer)(1.85 g) was obtained by reacting 1-D,L-propionyloxyethyl 7-amino-3-cephem-4-carboxylate (21 g) with the activated acid from diketene (6.4 ml) and bromine (14.75 g), and then reacting the resultant 1-D,L-propionyloxyethyl 7-(4-bromoacetoacetamido)-3-cephem-4-carboxylate with sodium nitrite (6.48 g), followed by reacting the resultant 1-D,L-propionyloxyethyl 7-(4-bromo-2-hydroxyiminoacetoacetamido)-3-cephem-4-carboxylate and thiourea (5.71 g) according to a similar manner to that of Example 3-(2).

IR (Nujol): 3270, 1780, 1745, 1660 cm$^{-1}$.

NMR (DMSO-$d_6$) δ: 1.03 (3H, t, J=8 Hz), 1.48 (2H, d, J=5 Hz), 2.37 (2H, q, J=8 Hz), 3.48–3.8 (2H, m), 5.15 (1H, d, J=5 Hz), 5.87 (1H, dd, J=8 Hz,5 Hz), 6.65 (1H, t, J=5 Hz), 6.67 (1H, s), 6.93 (1H, q, J=5 Hz), 7.08 (2H, broad s), 9.42 (1H, d, J=8 Hz), 11.33 (1H, broad s).

What we claim is:

1. A compound of the formula:

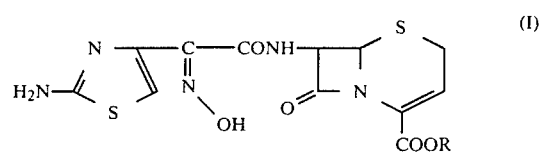

in which R is lower alkoxycarbonyloxy(lower)alkyl or 1-propionyloxyethyl, or a pharmaceutically acceptable acid addition salt thereof.

2. The compound of the claim 1, wherein R is 1-($C_1$-$C_3$)alkoxycarbonyloxy($C_1$-$C_3$)alkyl.

3. The compound of the claim 2, which is 1-ethoxycarbonyloxyethyl 7-[2-(2-aminothiazol-4-yl)-2-hydroxyiminoacetamido]-3-cephem-4-carboxylate (syn isomer).

4. The compound of the claim 1, which is 1-propionyloxyethyl 7-[2-(2-aminothiazol-4-yl)-2-hydroxyiminoacetamido]-3-cephem-4-carboxylate (syn isomer).

5. An antibacterial pharmaceutical composition which comprises, as an active ingredient, the compound of the claim 1 or a pharmaceutically acceptable acid addition salt thereof in admixture with pharmaceutically acceptable carriers.

6. A method for the treatment of infectious diseases caused by pathogenic microorganisms which comprises administering the compound of the claim 1 or a pharmaceutically acceptable acid addition salt thereof to infected human being or animals.

* * * * *